United States Patent [19]

Gray, Jr.

[11] Patent Number: 4,709,117

[45] Date of Patent: Nov. 24, 1987

[54] TOTAL ISOMERIZATION PROCESS AND APPARATUS

[75] Inventor: Robert L. Gray, Jr., Mahopac, N.Y.

[73] Assignee: Union Carbide Corporation, Danbury, Conn.

[21] Appl. No.: 849,064

[22] Filed: Apr. 7, 1986

[51] Int. Cl.[4] .............................................. C07C 5/13
[52] U.S. Cl. .................... 585/738; 422/129; 422/234
[58] Field of Search ................ 585/738; 422/129, 234

[56] References Cited

U.S. PATENT DOCUMENTS

| | | | |
|---|---|---|---|
| 3,150,205 | 9/1964 | Krane et al. | 585/738 |
| 3,309,415 | 3/1967 | Young et al. | 260/676 |
| 3,422,005 | 1/1969 | Avery | 208/310 |
| 3,475,345 | 10/1969 | Benesi | 252/455 |
| 3,527,835 | 8/1970 | Benesi | 260/683.65 |
| 3,615,188 | 9/1968 | Kouwenhoven et al. | 252/455 |
| 3,700,589 | 9/1970 | Symoniak et al. | 208/310 |
| 3,714,034 | 1/1973 | Kosseim et al. | 208/321 |
| 3,721,064 | 3/1973 | Symoniak et al. | 260/676 |
| 3,770,621 | 11/1973 | Collins et al. | 208/310 |
| 3,836,597 | 9/1974 | Sie | 260/683.65 |
| 3,842,114 | 10/1974 | Sie | 252/455 |
| 4,210,771 | 7/1980 | Holcombe | 585/701 |

FOREIGN PATENT DOCUMENTS 1064056 10/1979 Canada ............................ 260/713.1

Primary Examiner—Curtis R. Davis
Attorney, Agent, or Firm—Eugene Lieberstein

[57] ABSTRACT

Disclosed are a process and apparatus for virtually complete isomerization of normal paraffin hydrocarbons which reduces recycle rates and enables operation of reactors and adsorbers at more favorable conditions and otherwise improve operating efficiencies based on constant quantities of adsorbents and catalysts. Also, and according to a preferred embodiment, a process and apparatus are provided for utilizing reformer offgas as a hydrogen makeup in such a process wherein the offgas is first purified by a pressure swing adsorption apparatus. Reactor and adsorber pressures and recycle rates can be lowered due to higher concentration of hydrogen in the recycle stream and higher reactant concentrations in the reactor. Recycle capital and operating costs are greatly reduced.

56 Claims, 1 Drawing Figure

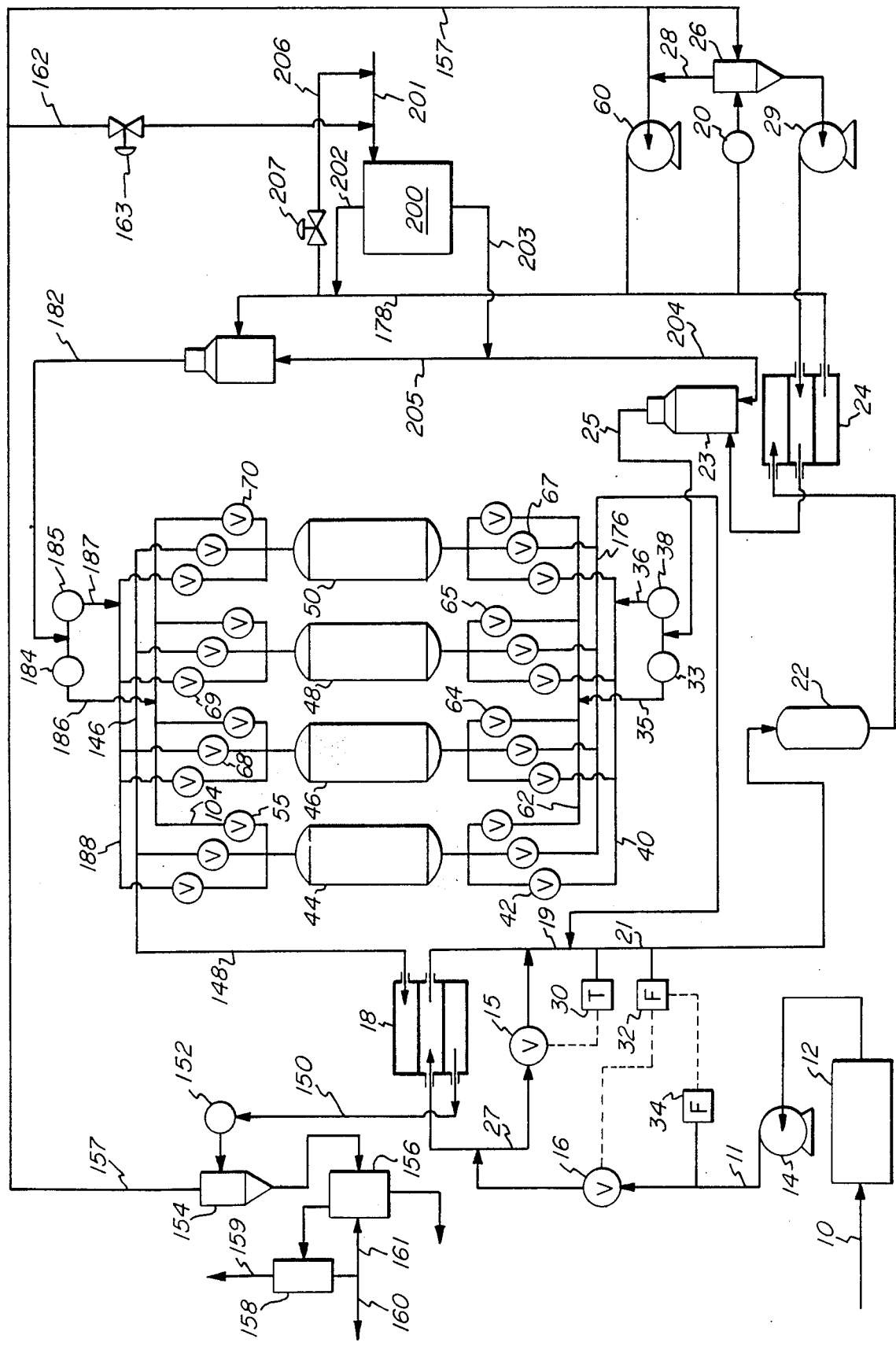

TOTAL ISOMERIZATION PROCESS AND APPARATUS

TECHNICAL FIELD

This invention relates to improvements in processing and apparatus for isomerizing normal paraffinic hydrocarbons by a catalytic total isomerization process.

The known total isomerization process for improving the octane rating of certain hydrocarbon fractions, especially mixed feedstocks containing normal and iso pentanes and hexanes, involves an initial catalytic reaction which must be conducted in the presence of hydrogen to protect the catalyst, and a separation procedure employing molecular sieve adsorbers. The adsorbers employ a hydrogen-containing purge gas stream to desorb normals and a recycle system to return desorbed normals and purge gas to the isomerization reactor.

The hydrogen in the recycled purge gas supplies a sufficient hydrogen partial pressure in the reactor which is required to prevent the deleterious effect of coking on catalyst life. By virtue of the recycle, the process will eventually totally isomerize all normal pentanes and hexanes in the feed. However, the purge gas and total recycle gas flow rates have been higher than desired, and it has been necessary to operate the adsorbers at pressures greater than optimum.

BACKGROUND ART

The operating pressure of total isomerization process (TIP) units, since the early 1970's, has typically been an economically dictated compromise of the optimum isomerization reactor and adsorber operating pressures.

The reactors have typically operated most efficiently at high pressures (300-400 psia) where the required hydrogen partial pressure can be met at a reasonably low recycle gas rate and compression ratio. Exemplary of teachings with regard to reactor conditions are those in U.S. Pat. No. 3,475,345 and U.S. Pat. No. 3,527,835 to Benesi, U.S. Pat. No. 3,615,188 to Kouwenhoven et al, and U.S. Pat. No. 3,842,114 to Sie.

Adsorber units, however, have typically operated more efficiently at lower pressures (200-250 psia) where the moles of stripping gas are more efficient and bed void storages of gas are lower. See in this regard U.S. Pat. No. 4,176,053 to Holcombe which calls for a non-sorbable purge gas, such as nitrogen, hydrogen, helium or methane, and specifically exemplifies a pressure of 250 psia.

Although adsorber and reactor units can perform over a wide range of pressures, to date, adsorption pressures in the range of 280 to 300 psia have been found to be at the optimum TIP compromise pressure for performance-based economics. In other words, this pressure range typically employed in the prior art was believed to economically satisfy both the reactor hydrogen partial pressure and the stripping requirements of the adsorber section.

Because the TIP units consume some hydrogen in the reactor and some is lost in solution and due to venting, makeup hydrogen must be added. Typically, this has been obtained from hydrogen-containing gas streams containing from 60 to 97 mole percent hydrogen and impurities. The higher purity stream, e.g., from steam reforming of methane, are typically more costly than desired and the more usual practice has been to employ catalytic reformer off gas streams which typically contain a major proportion of hydrogen, e.g., from 60 to 85 mole percent, and a minor proportion of light hydrocarbons, e.g., from 15 to 40 mole percent, with other impurities. The use of catalytic reformer off gas has generally been considered clean and favorable to the operation of the total isomerization process. However, the use of other, less pure hydrogen-containing refinery streams has been restricted due to the presence of larger amounts of light hydrocarbons and other impurities such as hydrogen sulfide, water, chlorides, and other impurities.

The predominant impurity in the typical prior art makeup gas streams is methane, along with decreasing amounts of ethane and propane, and butane (light hydrocarbons), and other impurities. The light hydrocarbons from the makeup gas, along with a smaller amount produced by cracking in the reactor, tend to build up in concentration within the recycle gas loop and adversely impact the selection of the TIP operating pressures and recycle gas rate. The other impurities, e.g., hydrogen sulfide, water, and chlorides, can be maintained at acceptable levels in the recycle by venting a small proportion of the stream as is necessary to control levels of total impurities in the recycle.

In Canadian Pat. No. 1,064,056, Reber et al describe a process for hydrocarbon separation and isomerization wherein large fluctuations in the concentration of either n-pentane or n-hexane in the reactor feed are prevented by suitably controlling the operation of a three bed adsorber system. According to the disclosure, no more than two beds are being desorbed at any given time and the terminal stage of desorption in one of the three beds is contemporaneous with the initial stage of desorption in another of the three beds.

The Canadian disclosure states the the hydrogen stream used as a purge gas in desorbing the adsorption bed and as the hydrogenation material in the isomerization reactor, need not be pure and is generally composed of one or a combination of two or more refinery hydrogen streams such as a reformer hydrogen and the like. It is disclosed that any impurities should be relatively non-sorbable and innert toward the adsorbent, catalyst and hydrocarbon. It is also disclosed that light hydrocarbons are produced in the catalytic unit, and that the recycle hydrogen stream is preferably at least 60 mole percent hydrogen.

The processes specifically exemplified by the Canadian patent employ "adsorber lead" flow wherein the fresh feed is first passed through the adsorbers to remove non-normal hydrocarbons prior to entering the reactor. This requires adsorbers of significantly increased size and larger recycle inventories. The exemplified reactor pressures of 220 psia require high hydrogen concentrations in the reactor to achieve a hydrogen partial pressure sufficient to protect the catalyst, and this in turn forces operation at lower than desired hydrocarbon reactant concentrations. The effluent from the reactor in Example 1 is disclosed as containing about 68 mole percent hydrogen and the feed in Example 2 is disclosed as containing about 60 mole percent hydrogen. With total pressure within the reactor exemplified at 220 psia, these high hydrogen concentrations and the presence of high quantities of light hydrocarbons in the recycle to the reactor leave room for only lower than desired concentrations of hydrocarbon reactants. Thus, while the Canadian process does employ low reactor total pressures, no gains due to decreased recycle rates are achieved, and the size of the adsorbers is increased. Moreover, these lower total pressures, combined with a lower concentration of reactants, results in a decreased reactant residence time within the reactor.

In U.S. Pat. No. 4,210,771, Holcombe describes a total isomerization process which reduces the recycle rate to the reactor while still maintaining a sufficient hydrogen partial pressure to protect the catalyst against coking. The partial pressure of the hydrogen in the reactor is a function of the hydrogen concentration. As with the earlier prior art, Holcombe's specifically disclosed recycle stream contains at least 50 mole percent hydrogen as well as desorbed normal paraffins and relatively non-sorbable light hydrocarbons. Some hydrogen is consummed during processing, some is lost due to solubility in the product and some is lost when venting to reduce levels of impurities from the recycle. As needed, reformer off gas is added to the recycle stream to make up hydrogen losses. The recycle stream must be introduced into the reactor at a sufficient rate to insure that a minimum hydrogen partial pressure is maintained at the worst case. The minimum hydrogen partial pressure required is dependent on the catalyst used, and is usually in the range of from 100 to 250 psia.

In the prior art to Holcombe, a constant fresh feed flow was employed and hydrogen flow rates for the worst case provided more than enough hydrogen as the desorbed normals flow rate decreased toward the end of a desorption cycle. The system of Holcombe maintains the flow rates of hydrogen in the recycle and the combined reactor feed at constant levels, and varies the flow rate of fresh feed in an inverse relationship with the desorbed normals in the recycle. By thus eliminating fluctuations in hydrocarbon flow rates to the reactor, the recycle flow rate to the reactor is reduced without risking an insufficient partial pressure of hydrogen to protect the catalyst.

It would be desirable, however, to yet further reduce recycle flow rates and operate reactors and adsorbers at more favorable conditions and to otherwise improve operating efficiencies based on constant quantities of adsorbants and catalysts.

SUMMARY OF THE INVENTION

The present invention provides a process and an apparatus for virtually completely isomerizing normal paraffin hydrocarbons in a feed stream containing normal and non-normal hydrocarbons, and in another aspect provides a process and apparatus for utilizing reformer off gas and other impure hydrogen-containing refinery streams as hydrogen sources in a process for virtually complete isomerization of normal paraffin hydrocarbons in a feed stream containing normal and non-normal hydrocarbons.

The invention enables the reduction of recycle rates for a total isomerization process without requiring any substantial increase in adsorber bed size; higher throughput of feed in an existing total isomerization process unit; reduction of catalyst requirements in the design of new total isomerization process units; the reduction of purge gas flow rates during desorption of normal hydrocarbons from molecular sieve adsorbers employed in a total isomerization process; the reduction of operating pressures for molecular sieve adsorbers employed in a total isomerization process; the maintenance of lower total pressure in the isomerization reactor of a total isomerization process; increasing the hydrogen concentration of the recycle stream in a total isomerization process; increasing the hydrogen concentration of the recycle stream in a total isomerization process by removing hydrocarbon impurities from a reformer gas prior to addition to the recycle as a source of makeup hydrogen; supplying from 50 to 100% of the heat requirements for a total isomerization process by burning hydrocarbon impurities removed from a reformer gas prior to its addition to the recycle as a source of makeup hydrogen; and reducing the hydrogen makeup requirements for a total isomerization process.

The process for virtually complete isomerization comprises: (a) passing a combined reactor feed comprising a fresh feed stream and a desorption effluent through an isomerization reactor containing an isomerization catalyst maintained under a hydrogen partial pressure sufficient to prevent coking of the isomerization catalyst at the reaction conditions maintained therein, to convert at least a portion of the normal hydrocarbons in said reactor feed to non-normal hydrocarbons which are withdrawn from the reactor in a reactor effluent; (b) separating reactor effluent into a hydrogen-rich gas stream and an adsorber feed stream; (c) passing the adsorber feed stream to an adsorption section containing an adsorber bed to adsorb normal hydrocarbons from said reactor effluent, and passing non-normal hydrocarbons out of the adsorption section as adsorber effluent containing an isomerate product; (d) forming a hydrogen recycle stream by adding essentially pure hydrogen to at least a portion of said hydrogen-rich gas stream in amounts sufficient to make up hydrogen losses; (e) passing said hydrogen recycle stream through said adsorber bed containing adsorbed normal hydrocarbons to produce said desorption effluent which comprises hydrogen and normal hydrocarbons; and (f) passing said desorption effluent to said isomerization reactor.

The apparatus for virtually complete isomerization comprises: (a) an isomerization reactor containing an isomerization catalyst; (b) means for passing a combined reactor feed through said isomerization reactor to convert at least a portion of the normal hydrocarbons in said reactor feed to non-normal hydrocarbons; (c) means for withdrawing non-normal hydrocarbons from the reactor in a reactor effluent; (d) means for separating reactor effluent into a hydrogen-rich gas stream and an adsorber feed stream; (e) an adsorber section containing an adsorber bed capable of adsorbing normal hydrocarbons; (f) means for passing the adsorber feed stream to said adsorption section to adsorb normal hydrocarbons from said reactor effluent; (g) means for passing non-normal hydrocarbons out of said adsorption section as adsorber effluent containing an isomerate product; (h) means for forming a hydrogen recycle stream by adding essentially pure hydrogen as makeup to at least a portion of said hydrogen-rich gas stream in an amount sufficient to make up hydrogen losses; (i) means for passing said hydrogen recycle stream through said adsorber bed containing adsorbed normal hydrocarbons to produce said desorption effluent which comprises hydrogen and normal hydrocarbons; and (j) means for passing said desorption effluent to said isomerization reactor.

The process for utilizing reformer off gas and other impure hydrogen-containing refinery streams as a hydrogen source in a process for virtually complete isomerization of normal paraffin hydrocarbons comprises: (a) separating isomerization reactor effluent into a hydrogen-rich gas stream and an adsorber feed stream; (b)

passing a hydrogen-containing refinery gas stream, comprising paraffinic hydrocarbon impurities, through a pressure swing adsorption system to yield essentially pure hydrogen and a second effluent containing paraffinic hydrocarbons; (c) forming a hydrogen recycle stream by adding said essentially pure hydrogen to at least a portion of said hydrogen-rich gas stream in an amount sufficient to make up hydrogen lost during processing; (d) passing said hydrogen recycle stream through an adsorber bed containing adsorbed normal hydrocarbon to produce a desorption effluent which comprises hydrogen and normal hydrocarbon; and (e) passing said desorption effluent to said isomerization reactor.

The apparatus for utilizing reformer off gas and other hydrogen-containing refinery streams as a hydrogen source in a process for virtually complete isomerization of normal paraffin hydrocarbons comprises: (a) means for separating isomerization reactor effluent into a hydrogen-rich gas stream and an adsorber feed stream; (b) a source of reformer offgas; (c) means for passing reformer offgas through a pressure swing adsorption system to yield essentially pure hydrogen and a second effluent containing paraffinic hydrocarbons; (d) means for forming a hydrogen recycle stream by adding said essentially pure hydrogen to at least a portion of said hydrogen-rich gas stream in an amount sufficient to make up hydrogen lost during processing; (e) means for passing said hydrogen recycle stream through an adsorber bed containing adsorbed normal hydrocarbon to produce a desorption effluent which comprises hydrogen and normal hydrocarbon; and (f) means for passing said desorption effluent to said isomerization reactor.

The amount of hydrogen makeup required for a total isomerization process is determined by processing losses in the isomerization reactor, where the degree of hydrocracking is influenced by high operating temperatures and pressures, solubility in product and direct venting. By adding makeup hydrogen in essentially pure form according to the present invention, the concentration of hydrogen in the hydrogen recycle stream is increased and the concentration of light hydrocarbons is decreased as compared to typical prior art operation. This allows reducing the flow rate of hydrogen recycle stream to the adsorbers and reactor and is a primary contributor to capital and energy savings, relative to the prior art.

The reduction in light hydrocarbon content of the hydrogen recycle stream also results in a lower average molecular weight of that stream. The lower molecular weight and the reduced flow rate allows equipment to be sized even smaller for equivalent pressure drops in a new installation and provides improved energy consumption due to reduced pressure drops for existing equipment.

The present invention, due to higher hydrogen and lower light hydrocarbon concentrations in the recycle and lower total recycle flow rates, enables the pressure within the isomerization reactor to be reduced, preferably to the range of from 220 to 250 psia, as compared to the typical commercial range of from 260 to 290 psia, permitting a reduction of from 20 to 40 psi. This reactor pressure reduction contributes some capital savings, but has as its major benefit the ability to operate the adsorber section at lower pressure. By operating the adsorber section at lower pressures, according to the invention, adsorber efficiency is unexpectedly increased to the point that no increase in the size of adsorber beds is required even though the flow rate of recycle gas for purging the adsorbers has been decreased. Without reducing the pressure in the adsorbers, it would be necessary to dramatically increase the size of the adsorber beds.

The increased hydrogen and decreased light hydrocarbon concentration in the recycle stream in combination with the decreased flow rate of that stream to the reactor also improves the performance of the reactor. The partial pressure of the normal paraffin reactants in the reactor can be increased according to the invention, as compared to the prior art, even though the absolute reactor pressure is decreased. Further, the reduction of concentration of light hydrocarbons fed to the reactor results in an increased residence time of reactants in the reactor. Both the longer residence time and increased reactant partial pressure can contribute to less catalyst requirements or less cracking, both of which in turn reduce makeup hydrogen requirements. Also, the increased residence time permits reactor operation at lower temperature, providing not only less cracking but an equilibrium more favorable to the production of the desired isomers.

DESCRIPTION OF THE DRAWING

The invention will be better understood and its advantages more apparent from the following detailed description when read in connection with the drawing, wherein:

The FIGURE is a schematic of a preferred process and apparatus arrangement according to the invention.

DETAILED DESCRIPTION

A mixed hydrocarbon feedstock (fresh feed) is fed via line 10 to an accumulator tank 12 from which it can be withdrawn by pump 14 as required for the process. The feedstock is fresh feed to the process and contains normal and non-normal hydrocarbons. It is composed principally of the various isomeric forms of saturated hydrocarbons having from five to six carbon atoms. The expansion "the various isomeric forms" is intended to denote all the branched chain and cyclic forms of the noted compounds, as well as the straight chain forms. Also, the prefix notations "iso" and "i" are intended to be generic designations of all branched chain and cyclic forms of the indicated compound.

Suitable feedstocks are typically obtained by refinery distillation operations, and may contain small amounts of $C_7$ and even higher hydrocarbons, but these are typically present, if at all, only in trace amounts. Olefinic hydrocarbons are advantageously less than about 4 mole percent in the feedstock. Aromatic and cycloparaffin molecules have a relatively high octane number, but are to a substantial degree cracked and/or converted into molecules of much lower octane number in the isomerization reactor. Accordingly, the preferred feedstock should not contain more than about 25 mole percent combined aromatic and cycloparaffinic hydrocarbons.

Advantageously, the $C_5$ and $C_6$ non-cyclic paraffins comprise at least 75, and preferably at least 85, mole percent of the feedstock, with at least 25, and preferably at least 35, mole percent of the feedstock being hydrocarbons selected from the group of n-pentane, n-hexane and combinations of these. Most desirably, the feedstock will comprise at least 40 mole percent of a combination of n-pentane and n-hexane. The following composition is typical of a feedstock suitable for processing according to the invention:

| Components | Weight % |
| --- | --- |
| $C_4$ and lower | 4.1 |
| i-$C_5$ | 24.5 |
| n-$C_5$ | 27.8 |
| i-$C_6$ | 27.4 |
| n-$C_6$ | 14.7 |
| $C_7$ and higher | 1.5 |

Referring again to the drawing, fresh feed is fed through line 10 to accumulator tank 12 from which it is drawn by pump 14 through control valve 16. The fresh feed may then pass to heat exchanger 18 where it is partially heated by heat exchange with effluent from an adsorption bed undergoing selective adsorption of normal hydrocarbons. The partially heated fresh feed from exchanger 18 passes through line 19 to line 21 where it combines with desorption effluent from an adsorption bed undergoing desorption of normal hydrocarbons. This desorption effluent will contain desorbed normal hydrocarbons, e.g., n-pentane and n-hexane, and hydrogen and light hydrocarbon and other impurities which comprise the purge gas used for desorption. The resulting combined reactor feed is passed to isomerization reactor 22.

The isomerization reactor 22 contains an isomerization catalyst which can be any of the various molecular sieve based catalyst compositions well known in the art which exhibit selective and substantial isomerization activity under the operating conditions of the process. As a general class, such catalysts comprise the crystalline zeolitic molecular sieves having an apparent pore diameter large enough to adsorb neopentane, $SiO_2/Al_2O_3$ molar ratio of greater than 3; less than 60, preferably less than 15, equivalent percent alkali metal cations and having those $AlO_4$-tetrahedra not associated with alkali metal cations either not associated with any metal cation, or associated with divalent or other polyvalent metal cations.

Because the feedstock may contain some olefins and will undergo at least some cracking, the zeolitic catalyst is preferably combined with a hydrogenation catalyst component, preferably a noble metal of group VIII of the Periodic classification of the Elements. The catalyst composition can be used alone or can be combined with a porous inorganic oxide diluent as a binder material. The hydrogenation agent can be carried either on the zeolitic component and/or on the binder. A wide variety of inorganic oxide diluent materials are known in the art—some of which exhibit hydrogenation activity per se. It will, accordingly, be understood that the expression "an inorganic diluent having a hydrogenation agent thereon" is meant to include both diluents which have no hydrogenation activity per se and carry a separate hydrogenation agent and those diluents which are per se hydrogenation catalysts. Oxides suitable as diluents, which of themselves exhibit hydrogenation activity, are the oxides of the metals of Group VI of the Mendeleev Periodic Table of Elements. Representative of the metals are chromium, molybdenum and tungsten.

It is preferred that the diluent material possess no pronounced catalytic cracking activity. The diluent should not exhibit a greater quantitative degree of cracking activity than the zeolitic component of the overall isomerization catalyst composition. Suitable oxides of this latter class are the aluminas, silicas, the oxides of metals of Groups III, IV-A and IV-B of the Mendeleev Periodic Table, and cogels of silica and oxides of the metals of the Groups III, IV-A and IV-B, especially alumina, zirconia, titania, thoria and combinations thereof. Aluminosilicate clays such as kaolin, attapulgite, sepiolite, polygarskite, bentonite, montmorillonite, and the like, when rendered in a pliant plastic-like condition by intimate admixture with water are also suitable diluent materials, particularly when said clays have not been acid-washed to remove substantial quantities of alumina.

Suitable catalysts for isomerization reactions are disclosed in detail in U.S. Pat. Nos. 3,236,761 and 3,236,762. A particularly preferred catalyst is one prepared from a zeolite Y (U.S. Pat. No. 3,130,007) having a $SiO_2/Al_2O_3$ molar ratio of about 5 by reducing the sodium cation content to less than about 15 equivalent percent by ammonium cation exchange, then introducing between about 35 and 50 equivalent percent of rare earth metal cations by ion exchange and thereafter calcining the zeolite to effect substantial deammination. As a hydrogenation component, platinum or palladium in an amount of about 0.1 to 1.0 weight percent can be placed on the zeolite by any conventional method. The disclosures of these above-cited U.S. patents are incorporated herein by reference in their entireties.

Depending on the particular catalyst composition employed, the operating temperature of the isomerization reactor is generally within the range of 200° to 390° C. and the pressure is within the range of 175 to 600 psia., desirably from 200 to 300, preferably 220 to 260 psia, and most preferably less than 250 psia. The reactor is maintained under a hydrogen partial pressure sufficient to prevent coking of the isomerization catalyst at the condition maintained in the reactor. Typically, the hydrogen partial pressure will be within the range of from 100 to 250, preferably from 110 to 160, psia with the hydrogen comprising from 45 to 70, preferably from 50 to 65, mole percent of the reactor contents which are maintained in a gaseous state.

The combined feed to the reactor will contain, in addition to hydrogen and hydrocarbon reactants, e.g., normal and iso pentane and hexane, a quantity of light hydrocarbons which are produced during the reaction and possibly as part of feed and makeup. Because these are non-sorbable, they are retained in the process at some equilibrium level and circulate with the recycle stream. Desirably, the concentration of light hydrocarbons, e.g., methane, ethane, propane and butane, is maintained under 20, preferably from 3 to 15 and most preferably less than 10, mole percent of the hydrogen recycle stream. This has the advantage that the concentration of light hydrocarbons in the reactor can be maintained at levels of less then 12, preferably less than 10 and most preferably from 2 to 7, mole percent.

By maintaining high concentrations of hydrogen, e.g., from 75 to 95 mole percent, and low concentrations of light hydrocarbons in the hydrogen recycle stream prior to desorption of normal hydrocarbons from the adsorber beds, the concentration of reactant hydrocarbons (e.g., $C_5$ and $C_6$ hydrocarbons) can desirably be maintained at a level of at least 20, preferably at least 25 and most preferably above 30, mole percent of the combined feed to the reactor. This enables improved reactor performance.

By thus increasing the concentration of reactant hydrocarbons in the combined feed, the reactor is able to operate at an increased reactant partial pressure. Because this increase in reactant hydrocarbon concentration is so great, as compared to the prior art, especially at the preferred reactor total pressures, the reactant partial pressures within the preferred range can be achieved even at the preferred low total reactor pressures defined above. Advantageously, even with the lower total reactor pressure, the combined effect of increased reactant partial pressures and reduced light hydrocarbons provides a longer residence time in the reactor which can contribute to better isomerization and/or lower catalyst inventories. The reaction converts at least a portion of the normal hydrocarbons in the combined feed to non-normal hydrocarbons.

It was disclosed in the Holcombe U.S. Pat. No. 4,210,771 that it is preferable to carry out the overall adsorption separation and isomerization process under essentially isobaric and isothermal conditions; however, the integration of the reactor and adsorption section into a total isomerization process has, in the past, necessitated a compromised but economically optimum, combined set of operating conditions which is less than optimum for either of the procedures. As will become apparent from the discussion herein, however, it is now possible to operate more efficiently at essentially isobaric and isothermal conditions with reduced total pressure and recycle loads. The present invention permits lower pressure operation of the reactor and the adsorption section with increased overall efficiencies in the total isomerization process. This is in sharp contrast with the prior art, where the purge gas and total recycle rates were higher than desired and necessitated pressures in the reactor which forced higher than optimum pressures to be employed throughout the process.

Referring again to the drawing, the effluent from the reactor 22 flows through heat exchanger 24 and water cooler 20 to separator 26, wherein it is separated into a hydrogen-rich gas stream and an adsorber feed stream. The hydrogen-rich gas stream is passed directly from separator 26 via line 28 to recycle compressor 60 and line 178. The adsorber feed is drawn from separator 26 by pump 29 and passes through exchanger 24 and line 25 to heater 23 where it is heated before passing to the separation section of the system. As will be explained in detail later, fuel for heater 23 can desirably be supplied by low-molecular weight hydrocarbons removed from a reformer offgas, or other hydrogen/hydrocarbon, stream which can be employed to supply makeup hydrogen to the process.

In the embodiment shown in the FIGURE, a bypass line 27 is provided around heat exchanger 18, and a temperature controller 30 is provided in line 21. Control valve 15 operates responsive to controller 30 to bypass fresh feed around the exchanger 18 and to control the heat added to the fresh feed.

In addition, in line 21 there is shown a flow controller 32 which, when employed, monitors the total combined reactor feed and which in turn operates control valve 16 to provide varying flow of fresh feed. A range control instrument 34 is shown located in line 11 between pump 14 and control valve 16 and monitors the flow rate of the fresh feed, computes average flow rates, compares the average to a point set on the instrument, and adjusts the set point on the combined reactor feed controller 32 to provide the desired average fresh feed flow rate. This system varies fresh feed in an inverse relationship with desorbed normals flow rate according to the process of Holcombe in U.S. Pat. No. 4,210,771, and can assure a constant flow rate of hydrocarbons to the reactor 22, where this is desired.

Adsorber feed from line 25 and exchanger 24 is directed partially to line 35 by way of pressure control valve 33 and partially to line 36 by means of flow rate control valve 38. From these lines, the adsorber feed stream is directed to the appropriate bed in the adsorption section.

The adsorber feed, containing normal and non-normal hydrocarbons in the vapor state is passed at superatmospheric pressure periodically in sequence through each of a plurality of fixed adsorber beds, e.g., four as described in U.S. Pat. No. 3,700,589 or three as described in U.S. Pat. No. 3,770,621, of an adsorption section containing a zeolitic molecular sieve adsorbent. These U.S. patents are incorporated by reference herein in their entireties. Preferably, the adsorbents have effective pore diameters of substantially 5 Angstroms. In a four bed system, each of the beds cyclically undergoes the stages of:

A-1 adsorption-fill, wherein the vapor in the bed void space consists principally of a non-sorbable purge gas and the incoming feedstock forces the said non-sorbable purge gas from the bed void space out of the bed without substantial intermixing thereof with non-adsorbed feedstock fraction.

The term "bed void space" for purposes of this description means any space in the bed not occupied by solid material except the intracrystalline cavities of the zeolite crystals. The pores within any binder material which may be used to form agglomerates of the zeolite crystals is considered to be bed void space.

A-2 adsorption, wherein the feedstock is cocurrently passed through said bed and the normal constituents of the feedstock are selectively adsorbed into the internal cavities of the crystalline zeolitic adsorbent and the nonadsorbed constituents of the feedstock are removed from the bed as an effluent having a greatly reduced content of non-feedstock constituents;

D-1 void space purging, wherein the bed loaded with normals adsorbate to the extent that the stoichiometric point of the mass transfer zone thereof has passed between 85 and 97 percent of the length of the bed and containing in the bed voids space a mixture of normals and non-normals in essentially feedstock proportions, is purged countercurrently, with respect to the direction of A-2 adsorption by passing through the bed a stream of a non-sorbable purge gas in sufficient quantity to remove said void space feedstock vapors but not more than that which produces about 50 mole percent, preferably not more than 40 mole percent, of adsorbed feedstock normals in the bed effluent; and D-2 purge desorption, wherein the selectively adsorbed feedstock normals are desorbed as part of the desorption effluent by passing a non-sorbable purge as countercurrently with respect to A-2 adsorption through the bed until the major proportion of adsorbed normals has been desorbed and the bed void space vapors consist principally of non-sorbable purge gas, e.g., a hydrogen recycle stream which comprises hydrogen and light hydrocarbons.

The zeolitic molecular sieve employed in the adsorption bed must be capable of selectively adsorbing the normal paraffins of the feedstock using molecular size and configuration as the criterion. Such a molecular sieve should, therefore, have an apparent pore diameter of less than about 6 Angstroms and greater than about 4 Angstroms. A particularly suitable zeolite of this type is zeolite A, described in U.S. Pat. No. 2,883,243, which in several of its divalent exchanged forms, notably the calcium cation form, has an apparent pore diameter of about 5 Angstroms, and has a very large capacity for adsorbing normal paraffins. Other suitable molecular sieves include zeolite R, U.S. Pat. No. 3,030,181; zeolite T, U.S. Pat. No. 2,950,952, and the naturally occurring, zeolitic molecular sieves chabazite and erionite. These U.S. patents are incorporated by reference herein in their entireties.

The term "apparent pore diameter" as used herein may be defined as the maximum critical dimension, or the molecular species which is adsorbed by the adsorbent under normal conditions. The critical dimension is defined as the diameter of the smallest cylinder which will accommodate a model of the molecule constructed using the available values of bond distances, bond angles and van der Waals' radii. The apparent pore diameter will always be larger than the structural pore diameter, which can be defined as the free diameter of the appropriate silicate ring in the structure of the adsorbent.

Referring again to the drawing, and the adsorption section in particular, the following description details an operation wherein bed 44 is undergoing A-1 adsorption-fill; bed 46, A-2 adsorption; bed 48, D-1 void space purging; and bed 50, D-2 purge desorption. A portion of the adsorber feed from line 25 is directed via line 36 through manifold 40 and valve 42 to adsorption bed 44 undergoing A-1 adsorption. Each of the four adsorption beds in the system, namely beds 44, 46, 48 and 50 contain a molecular sieve adsorbent in a suitable form such as cylindrical pellets.

Bed 44, at the time that feed passing through valve 42 enters, contains residual hydrogen-containing purge gas from the preceding desorption stroke. As will be explained in detail later, the hydrogen-containing purge gas is supplied to the adsorbers during desorption as a hydrogen recycle stream via line 182. The rate of flow of the adsorber feed through line 36, manifold 40 and valve 42 is controlled such that bed 44 is flushed of residual hydrogen-containing purge gas uniformly over a period of about two minutes.

During this first stage of adsorption in bed 44, the hydrogen-containing purge gas effluent passes from the bed through valve 55 into manifold 104. During the two minute period when the hydrogen-containing purge gas was being flushed from bed 44, the remaining adsorber feed passes through valve 33 and line 35, through manifold 62, and valve 64 to bed 46.

The normal paraffins in the feed are adsorbed by bed 46 undergoing A-2 adsorption and an adsorber effluent containing an isomerate product, i.e., the non-adsorbed non-normals, emerges from the bed through valve 68 and from there is fed to manifold 146. The adsorber effluent flows through line 148, heat exchanger 18, line 150, water cooler 152, to separator 154, and the condensed product is accumulated in accumulator 156. A stabilizer 158, which typically comprises a refux column with overhead water cooling, draws condensed product from the accumulator, removes hydrogen and other low-boiling materials via vent 159 and discharges product via line 160 or returns it to accumulator 156 via line 161.

The hydrogen and low-boiling materials removed via vent 159 can be employed directly as fuel for heaters 23 and 180, or can be passed to hydrogen purification unit 200, preferably a pressure swing adsorption system, as will be described in greater detail.

Residual hydrogen-containing purge gas in the adsorber effluent leaves separator 154 through line 157, to recycle compressor 60. During the two minute period when the residual hydrogen-containing purge gas is being flushed from bed 44, i.e., A-1 adsorption, bed 48 is undergoing the first stage of purging with the hydrogen recycle stream wherein the hydrocarbons in the bed void space are being flushed from the bed, i.e., D-1 purging. During the same two minute interval, bed 50 is undergoing the second stage of desorption, i.e., D-2 purge desorption, in which the normal hydrocarbons are desorbed from the molecular sieve adsorbent using hydrogen recycle (purge gas) stream and removed from the bed.

From compressor 60, the hydrogen-containing gas stream from separator 154 is passed through line 178 and heater 180, wherein it is heated and then passed through line 182 as the hydrogen recycle stream, which according to present invention can have a hydrogen content of from 75 to 95%, preferably at least 80 and most preferably at least 85, mole percent. And, as discussed above, the concentration of light hydrocarbons and other impurities will be maintained at lower levels. The pressure of the adsorbers will typically be within the range of from 200 to 320 psia, and preferably will be in the range of from 240 to 275 psia. These preferred pressures are lower than typically employed in total isomerization processing according to the prior art, and the concentration of hydrogen in the recycle stream is higher. This enables lower flow rates to the adsorbers with no diminution of adsorption and no significant increase in adsorption bed volumes. These advantages will be discussed in greater detail below.

The hydrogen recycle stream from line 182 can be divided into two streams by means of flow control valves 184 and 185, and the lesser stream passed through line 187, manifold 188, and valve 69 countercurrently (with respect to the previous adsorption stroke) through bed 48. The low, controlled flow rate employed for the two minute first stage desorption is for the purpose of flushing non-adsorbed hydrocarbons from the bed voids without causing excessive desorption of the normals from the adsorbent. The effluent from bed 48, passes through valve 65 and into manifold 62 where it is recycled through valve 64 directly to bed 46 undergoing A-2 adsorption. The major portion of the hydrogen recycle stream from line 182 is passed through control valve 184, line 186, to manifold 104 where it is mixed with the previously mentioned first stage adsorption effluent from valve 55 and then passes through valve 70 and bed 50. During this period, selectively adsorbed normal paraffins are desorbed from the zeolitic molecular sieve and flushed from the bed. The adsorption effluent from bed 50, comprising hydrogen and desorbed normal paraffins, passes through valve 67 and manifold 176 to line 21, where it is mixed with incoming fresh feed.

The foregoing description is for a single two minute period of a total eight minute preferred cycle for the system. For the next two minute period, appropriate valves are operated so that bed 44 begins A-2 adsorption, bed 46 begins D-1 purging, bed 48 begins D-2 desorption, and bed 50 begins A-1 adsorption. Similarly, a new cycle begins after each two minute period and at the end of an eight minute period all the beds have gone through all stages of adsorption and desorption.

The following chart indicates the functioning of each of the four beds for each two minute period:

| Time, min. | 0-2 | 2-4 | 4-6 | 6-8 |
|---|---|---|---|---|
| Bed 44 | A-1 | A-2 | D-1 | D-2 |
| Bed 46 | A-2 | D-1 | D-2 | A-1 |
| Bed 48 | D-1 | D-2 | A-1 | A-2 |
| Bed 50 | D-2 | A-1 | A-2 | D-1 |

The isomerization process will result in some hydrogen losses due to hydrogenation of starting materials and cracked residues. Hydrogen will also be lost due to solubility in product, from the stabilizer vent 159 and possibly a vent from line 157, say at line 162 which can be controlled by valve 163. These losses require the addition of makeup hydrogen. In the past, makeup hydrogen has been supplied in impure form, typically as an offgas from catalytic reforming or steam reforming of methane. These hydrogen sources have been considered to be suitably pure for total isomerization processes which have typically required a vent from the recycle stream. However, refinery streams of lesser purity have been considered unsatisfactory. It is an advantage of the present invention that catalytic reformer offgas with a hydrogen concentration of 85 mole percent or less can be employed. Indeed, relatively impure hydrogen-containing refinery streams can be employed. These will typically contain a major proportion of hydrogen, but very significant levels, e.g., from 15 to 40 mole percent of light hydrocarbons as well as other impurities such as hydrogen sulfide, chloride and water.

According to the present invention, makeup hydrogen is supplied in essentially pure form from a suitable source, which preferably will be a unit such as a pressure swing adsorption apparatus or other suitable hydrogen purification unit 200. Typical of these units and their operations are those described in U.S. Pat. No. 3,986,849, the disclosure of which is hereby incorporated by reference.

As shown in the drawing, impure hydrogen-containing gas is fed to unit 200 via line 201. Essentially pure, e.g., at least 98, and preferably 99 plus, mole percent hydrogen is fed to the hydrogen-rich gas stream in line 178 via line 202. Lesser purity hydrogen can be employed for limited periods, if required, such as during downtime for the unit 200 or a portion of it. The unit 200 preferably purifies the hydrogen by removing light hydrocarbons, herein hydrocarbons, hydrogen sulfide, chlorides and water. A second effluent from unit 200 containing light hydrocarbons, which are removed from the impure hydrogen feed to the unit 200, is passed as a low pressure stream, e.g., 17 to 75 psia, via line 203 to lines 204 and 205 which supply fuel to heaters 23 and 180. Preferably, from 50 to 100% of the heat requirements of the total isomerization process will be supplied by this second effluent.

As noted earlier, the hydrogen-containing stream from stabilizer vent 159 and as well as vent stream 162 from line 157 can be fed to unit 200 to provide purified hydrogen for makeup in the hydrogen recycle stream and to provide fuel for heaters 23 and 180, respectively. If desired, impure hydrogen can also be drawn from line 178 via line 206 and control valve 207 and fed to unit 200 via line 201.

The process will preferably be controlled in an integrated manner, employing a computer to monitor and set each of the various valves which control flow rates, the control being effective to stabilize total as well as hydrogen partial pressure in the reactor within the ranges noted above. Also, the control valves 163 and 207, which control the amount of vent from recycled gas streams are preferably integrated with overall process control to achieve the desired hydrogen concentrations in the recycle and the reactor as well as the maintenance of the required, hydrogen partial pressure in the reactor. According to one embodiment, the flow rate of hydrogen-rich gas stream separated from the reactor effluent is measured by suitable means and passed to a computer; and from this value and, if necessary, measured values of other process parameters, particularly pressures, a rate of addition for makeup hydrogen necessary to achieve said sufficient hydrogen partial pressure in the reactor is derived. According to a simplified embodiment, the presence of the hydrogen-rich gas stream flow rate is sensed as the sole criteria for adding makeup hydrogen.

Typically, commercial operation of total isomerization processes has called for use of catalytic reformer offgas as a source of makeup hydrogen. The gas typically contains from 85 to 65 mole percent hydrogen and from 8 to 30 mole percent total methane, ethane and propane. By replacing this reformer offgas with essentially pure hydrogen, the total isomerization process can be optimized at a lower total pressure where reactor and adsorber performance are improved, while still maintaining the required hydrogen partial pressure at the reactor at efficiently high concentrations of hydrocarbon reactants. The overall result is a more economical process. And, an advantage of the present invention is that gas streams of lesser purity then catalytic reformer offgas can be employed as a feed stream for makeup hydrogen.

The use of purified makeup hydrogen according to the invention dramatically increases the hydrogen concentration in the hydrogen recycle stream from about 65-70 mole percent when employing catalytic reformer offgas according to the prior art procedures, even with a vent of about 5 volume percent of the stream to remove impurities, to greater than 75, preferably at least 80 and most preferably at least 85, mole percent according to the invention, even with no vent of gas from the recycled hydrogen-containing stream. This reduces the mass flow rate of the hydrogen recycle stream. The adsorber section can then be operated at a lower, more optimum pressure with a reduced stripping gas rate, while still maintaining the required hydrogen partial pressure at the reactor.

The purified makeup hydrogen simplifies the design procedure and improves the operability of the actual unit. During the design phase, only one makeup gas composition has to be considered. This will eliminate the overdesign of equipment, for a low purity case the refiner will only occasionally operate at. Also, by allowing the hydrogen purification unit to take the fluctuations in makeup gas composition, the process can operate without the presently required occasional adjustments to control the hydrogen partial pressure. The hydrogen purification unit will actually remove the risk that the refiner will mis-operate the unit during end-of-run reformer conditions.

In one example of the improvements which can be realized according to the invention, one commercial total isomerization process (TIP), as originally designed, uses an adsorption pressure of 280 psia and a recycle hydrogen rate of 5400 lb. moles/hr. (65% $H_2$ with a 5% of recycle loop vent) to maintain the following conditions in the reactor at 260 psia:

|  | Mole Percent | Partial Pressure (psia) |
| --- | --- | --- |
| Hydrogen | 55 | 143 |
| Light hydrocarbons | 27 | 70 |
| Hydrocarbon reactants | 18 | 47 |

By using a pressure swing adsorption unit to purify the makeup gas before it enters the TIP unit, the adsorption pressure can be reduced to 245 psia, and the hydrogen recycle rate can be reduced to 4000 lb. moles/hr. (82% $H_2$ with no venting required) and the following conditions will be maintained in the reactor at 225 psia:

|  | Mole Percent | Partial Pressure (psia) |
| --- | --- | --- |
| Hydrogen | 60 | 135 |
| Light hydrocarbons | 10 | 22 |
| Hydrocarbon reactants | 30 | 68 |

The savings associated with both the reduced recycle gas rate and pressure can be attained with little to no increase in adsorbent inventory, primarily due to the lower operating pressure. At the lower pressure, the moles of purge gas become more efficient due to the increase in actual volume of gas. In addition, the void storage of normals and non-normals in the vessel at the end of the adsorption step is less. Therefore, the amount of normals recycled back to the feed step during the D-1 counter-current to feed step (void purge) is less at the lower pressure.

A reduction in adsorption pressure of 35 psi can result in a 14% reduction in the vessel void volume rate, which in turn can reduce the D-1 recycle to feed. Also contributing to the adsorption section improvement is a lower D-1 feed requirement, a small reduction in the normal paraffin rate to the adsorbers (primarily $nC_4$) and a small reduction in the vessel void fraction due to a higher L/D design of the vessel.

An added effect of purifying the makeup hydrogen prior to entering the TIP unit is the elimination of hydrochloric acid from the catalytic reformer offgas which usually contains from 2 to 10 ppmv of HCl. This acid will react with the alumina in the molecular sieve structure and cause a loss in crystallinity. A general "rule of thumb" is that 5 to 8 lbs. of sieve will be destroyed by 1 lb. of chlorine. In present design this loss is reduced and bed volumes can be reduced by any amount previously employed as a contingency.

The above description is for the purpose of teaching the person of ordinary skill in the art how to practice the present invention and is not intended to detail all those obvious modifications and variations of it which will become apparent to the skilled worker upon reading the description. It is intended, however, that all such obvious modifications and variations be included within the scope of the present invention which is defined by the following claims.

I claim:

1. A process for virtually complete isomerization of normal paraffin hydrocarbons in a feed stream containing normal and non-normal hydrocarbons, comprising:
   (a) passing a combined reactor feed comprising said feed stream and a desorption effluent, as hereinafter delineated, through an isomerization reactor containing an isomerization catalyst maintained under a hydrogen partial pressure sufficient to prevent coking of the isomerization catalyst at the reaction conditions maintained therein, to convert at least a portion of the normal hydrocarbons in said reactor feed to non-normal hydrocarbons which are withdrawn from the reactor in a reactor effluent;
   (b) separating reactor effluent into a hydrogen-rich gas stream and an adsorber feed stream;
   (c) passing the adsorber feed stream to an adsorption section containing an adsorber bed to adsorb normal hydrocarbons from said reactor effluent, and passing non-normal hydrocarbons out of the adsorption section as adsorber effluent containing an isomerate product;
   (d) forming a hydrogen recycle stream by adding essentially pure hydrogen to at least a portion of said hydrogen-rich gas stream in an amount sufficient to make up hydrogen lost during processing;
   (e) passing said hydrogen recycle stream through said adsorber bed containing adsorbed normal hydrocarbons to produce said desorption effluent which comprises hydrogen and normal hydrocarbons; and
   (f) passing said desorption effluent to said isomerization reactor.

2. A process according to claim 1 including the step of separating said hydrogen-rich gas stream into a vent stream and a recycle stream.

3. A process according to claim 2 including the further step of burning the content of the vent stream to supply heat to at least one feed to said adsorption section.

4. A process according to claim 2 including the steps of passing the vent stream through a pressure swing adsorption system to produce essentially pure hydrogen and combining said hydrogen with said hydrogen recycle stream.

5. A process according to claim 1 which further includes the step of controlling said hydrogen recycle stream and said adsorber feed stream flow rates to said adsorption section and the desorption effluent therefrom to operate said adsorbers at a pressure of from 240 to 275 psia.

6. A process according to claim 5 wherein said hydrogen partial pressure in said reactor is within the range of from 10 to 160 psia and the concentration of hydrogen in said hydrogen recycle stream is at least 75 mole percent.

7. A process according to claim 6 wherein the isomerization reactor is maintained at a total pressure of from 220 to 260 psia.

8. A process according to claim 7 which further includes controlling the addition of essentially pure hydrogen to said hydrogen-rich gas stream to provide said hydrogen partial pressure within said isomerization reactor and to maintain the concentration of hydrogen in said recycle stream at a level of at least 80 mole percent and the concentration of light hydrocarbons in said recycle stream at a level of less than 20 mole percent.

9. A process according to claim 5 wherein said hydrogen partial pressure in said reactor is within the range of from 110 to 160 psia and the isomerization reactor is maintained at a total pressure of from 220 to 260 psia.

10. A process for virtually complete isomerization of normal paraffin hydrocarbons in a feed stream containing normal and non-normal hydrocarbons, comprising:
   (a) passing a combined reactor feed comprising said feed stream and a desorption effluent, as hereinafter delineated, through an isomerization reactor containing an isomerization catalyst maintained under a sufficient hydrogen partial pressure to prevent coking of the isomerization catalyst at the reaction conditions maintained therein, to convert at least a portion of the normal hydrocarbons in said reactor feed to non-normal hydrocarbons which are withdrawn from the reactor in a reactor effluent;
   (b) separating the reactor effluent into a hydrogen-rich gas stream and an adsorber feed stream;
   (c) passing the adsorber feed stream to an adsorption section containing an adsorber bed to adsorb normal hydrocarbons from said reactor effluent, and passing non-normal hydrocarbons out of the adsorption section as adsorber effluent containing an isomerate product;
   (d) passing a makeup feed stream containing hydrogen and hydrocarbons through a pressure swing adsorption system to produce an essentially-pure hydrogen makeup stream;
   (e) forming a hydrogen recycle stream by combining said essentially pure hydrogen makeup stream with at least a portion of said hydrogen-rich gas stream in relative amounts sufficient to achieve a hydrogen concentration of at least 75 mole percent hydrogen and less than 20 mole percent light hydrocarbons in said hydrogen recycle stream;
   (f) passing said hydrogen recycle stream through said adsorber bed containing adsorbed normal hydrocarbons to produce said desorption effluent which comprises hydrogen and normal hydrocarbons; and
   (g) passing said desorption effluent to said isomerization reactor.

11. A process according to claim 10 wherein said makeup hydrogen-containing stream is a catalytic reformer off gas.

12. A process according to claim 11 wherein said reformer off gas comprises a major proportion of hydrogen and a minor proportion of paraffinic hydrocarbons.

13. A process according to claim 10 wherein said pressure swing adsorption system further produces a second effluent containing paraffinic hydrocarbons.

14. A process according to claim 13 wherein said second effluent is burned to supply heat to at least one feed to heaters for said adsorption section.

15. A process according to claim 10 wherein said adsorption section is operated at pressures within the range of from 200 to 275 psia.

16. A process according to claim 10 including the step of separating said hydrogen-rich gas stream into a vent stream and a recycle stream.

17. A process according to claim 16 including the further step of burning the content of the vent stream to supply heat to at least one feed.

18. A process according to claim 16 including the steps of passing the vent stream through a multi-bed pressure swing adsorption system to produce essentially pure hydrogen and combining it with said hydrogen recycle stream.

19. A process according to claim 10 wherein said hydrogen partial pressure is within the range of from 110 to 160 psia and the isomerization reactor is maintained at a total pressure of from 220 to 260 psia.

20. A process for virtually complete isomerization of normal paraffin hydrocarbons in a feed stream containing normal and non-normal hydrocarbons, comprising:
   (a) passing a combined reactor feed comprising said feed stream and a desorption effluent, as hereinafter delineated, through an isomerization reactor to convert at least a portion of the normal hydrocarbons in said reactor feed to non-normal hydrocarbons, said reactor containing an isomerization catalyst maintained under a sufficient hydrogen partial pressure to prevent coking of the isomerization catalyst at the reaction conditions maintained therein which are withdrawn from the reactor in a reactor effluent;
   (b) separating reactor effluent into a hydrogen-rich gas stream and an adsorber feed stream;
   (c) passing the adsorber feed stream to an adsorption section to adsorb normal hydrocarbons from said reactor effluent, and passing non-normal hydrocarbons out of the adsorption section as adsorber effluent containing an isomerate product;
   (d) separating said hydrogen-rich gas stream into a hydrogen vent stream and a hydrogen-rich recycle stream;
   (e) measuring the flow of said hydrogen-rich recycle stream;
   (f) deriving from the measured flow of hydrogen-rich recycle stream a rate for makeup hydrogen necessary to achieve said sufficient hydrogen partial pressure in said isomerization reactor;
   (g) forming a hydrogen recycle stream by adding essentially pure makeup hydrogen to at least a portion of said hydrogen-rich gas stream at the derived rate necessary to achieve a hydrogen concentration of at least 80 mole percent and a concentration of light hydrocarbons of from 3 to 15 mole percent in said hydrogen recycle stream;
   (h) passing said hydrogen recycle stream through said adsorber bed to produce said desorption effluent which comprises hydrogen and normal hydrocarbons; and
   (i) passing said desorption effluent to said isomerization reactor.

21. A process according to claim 20 including the step of separating said hydrogen-rich gas stream into a vent stream and a recycle stream.

22. A process according to claim 21 including the further step of burning the content of the vent stream to supply heat to at least one feed stream.

23. A process according to claim 21 including the steps of passing the vent stream through a pressure swing adsorption system to produce essentially pure hydrogen and combining said hydrogen with said hydrogen recycle stream.

24. A process according to claim 20 wherein said hydrogen partial pressure in said reactor is within the range of from 110 to 160 psia.

25. A process according to claim 24 wherein the isomerization reactor is maintained at a total pressure of from 210 to 260 psia.

26. A process according to claim 20 including the further step of producing said essentially pure makeup hydrogen by passing a reformer off gas, comprising a major proportion of hydrogen and a minor proportion of paraffinic hydrocarbons, through a pressure swing adsorption system to yield said essentially pure hydrogen and a second effluent containing paraffinic hydrocarbons.

27. A process according to claim 26 wherein said second effluent is burned to supply heat to at least one feed to said adsorption section.

28. A process according to claim 20 wherein said adsorption section is operated at pressures of from 200 to 275 psia.

29. A process according to claim 28 wherein said hydrogen partial pressure in said reactor is within the range of from 110 to 160 psia and the isomerization reactor is maintained at a total pressure of from 220 to 260 psia.

30. A process for virtually complete isomerization of normal paraffin hydrocarbons in a feed stream containing normal and non-normal hydrocarbons, comprising:
(a) passing a combined reactor feed comprising at least 20 mole percent reactant hydrocarbons, through an isomerization reactor to convert at least a portion of the normal hydrocarbons in said reactor feed to non-normal hydrocarbons which are withdrawn from said reaction in a reactor effluent, said reactor containing an isomerization catalyst maintained under a hydrogen partial pressure of from 110 to 160 psia and a total pressure of from 220 to 260 psia;
(b) separating the reactor effluent into a hydrogen-rich gas stream and an adsorber feed stream;
(c) passing the adsorber feed stream to an adsorption section operated at pressures of from 240 to 275 psia to adsorb normal hydrocarbons from said reactor effluent, and passing non-normal hydrocarbons out of the adsorption section as adsorber effluent containing an isomerate product;
(d) forming a hydrogen recycle stream by adding essentially pure hydrogen to at least a portion of said hydrogen-rich gas stream in an amount sufficient to achieve a hydrogen concentration of at least 75 mole percent and a light hydrocarbon concentration of less than 20 mole percent in said hydrogen recycle stream;
(e) passing said hydrogen recycle stream through said adsorber bed to produce said desorption effluent which comprises hydrogen and normal hydrocarbons; and
(f) passing said desorption effluent to said isomerization reactor.

31. A process according to claim 30 including the step of separating said hydrogen-rich gas stream into a vent stream and a recycle stream.

32. A process according to claim 31 including the further step of burning the content of the vent stream to supply heat to at least one feed to said adsorption section.

33. A process according to claim 31 including the steps of passing the vent stream through a pressure swing adsorption system to produce essentially pure hydrogen and combining said hydrogen with said hydrogen recycle stream.

34. A process according to claim 30 including the further step of producing said essentially pure hydrogen by passing a catalytic reformer off gas, comprising a major proportion of hydrogen and a minor proportion of paraffinic hydrocarbons, through a pressure swing adsorption system to yield said essentially pure hydrogen and a second effluent containing paraffinic hydrocarbons.

35. A process according to claim 34 wherein said second effluent is recycled to said adsorption section.

36. A process according to claim 34 wherein said second effluent is burned to supply heat to at least one feed to said isomerization reactor.

37. A process according to claim 30 which further includes the step of controlling the feed of said hydrogen recycle stream and said adsorber feed stream to said adsorption section and the desorption effluent therefrom to provide said hydrogen partial pressure within said isomerization reactor.

38. A process according to claim 37 which further includes controlling the addition of essentially pure hydrogen to said hydrogen-rich gas stream to provide said hydrogen partial pressure within said isomerization reactor.

39. A process according to claim 38 including the further step of producing said essentially pure hydrogen by passing a catalytic reformer off gas, comprising a major proportion of hydrogen and a minor proportion of paraffinic hydrocarbons, through a pressure swing adsorption system to yield said essentially pure hydrogen and a second effluent containing paraffinic hydrocarbons.

40. A process for utilizing a catalytic reformer off gas as a hydrogen source in a process for virtually complete isomerization of normal paraffin hydrocarbons in a feed stream containing normal and non-normal hydrocarbons, comprising:
(a) combining said feed stream and a desorption effluent, as hereinafter delineated, to obtain a combined reactor feed comprising at least 25 mole percent of reactant hydrocarbons;
(b) passing said combined reactor feed through an isomerization reactor to convert at least a portion of the normal hydrocarbons in said reactor feed to non-normal hydrocarbons which are withdrawn from said reactor in a reactor effluent, said reactor containing an isomerization catalyst maintained under a hydrogen partial pressure of from 110 to 160 psia and a total pressure of from 220 to 260 psia;
(c) separating reactor effluent into a hydrogen-rich gas stream and an adsorber feed stream;
(d) passing the adsorber feed stream to an adsorption section operated at pressures of from 200 to 320 psia to adsorb normal hydrocarbons from said reactor effluent, and passing non-normal hydrocarbons out of the adsorption section as adsorber effluent containing an isomerate product;
(e) passing a catalytic reformer off gas, comprising a major proportion of hydrogen and a minor proportion of paraffinic hydrocarbons, through a pressure swing adsorption system to yield said essentially pure hydrogen and a second effluent containing paraffinic hydrocarbons;
(f) burning said second effluent to supply heat to at least one feed to said adsorption section; and
(g) forming a hydrogen recycle stream having a hydrogen concentration of at least 80 mole percent and a light hydrocarbon concentration of from 3 to 15 mole percent by adding said essentially pure hydrogen to at least a portion of said hydrogen-rich gas stream in an amount sufficient to achieve said concentrations and hydrogen partial pressure in said reactor when recycled to said isomerization reactor;
(h) passing said hydrogen recycle stream through said adsorber bed to produce said desorption effluent which comprises hydrogen and normal hydrocarbons; and (i) passing said desorption effluent to said isomerization reactor.

41. A process according to claim 40 which further includes the step of controlling said hydrogen recycle stream and said adsorber feed stream flow rates to said adsorption section and the desorption effluent therefrom to provide said hydrogen partial pressure within said isomerization reactor.

42. A process according to claim 41 which further includes controlling the addition of essentially pure hydrogen to said hydrogen-rich gas stream to provide said hydrogen partial pressure within said isomerization reactor.

43. A process according to claim 40 including the step of separating said hydrogen-rich gas stream into a vent stream and a recycle stream.

44. A process according to claim 41 including the further step of burning the content of the vent stream to supply heat to at least one feed to said adsorption section.

45. A process according to claim 41 including the steps of passing the vent stream through a multi-bed pressure swing adsorption system to produce essentially pure hydrogen and combining said hydrogen with said hydrogen recycle stream.

46. A process for utilizing a catalytic reformer off gas as a hydrogen source in a process for virtually complete isomerization of normal paraffin hydrocarbons in a feed stream containing normal and non-normal hydrocarbons, comprising:

(a) passing a combined reactor feed of said feed stream and a desorption effluent, as hereinafter delineated, through an isomerization reactor to convert at least a portion of the normal hydrocarbons in said reactor feed to non-normal hydrocarbons which are withdrawn from said reactor in a reactor effluent, said reactor containing an isomerization catalyst maintained under a hydrogen partial pressure of from 110 to 160 psia, a partial pressure of $C_5$ and higher hydrocarbons of from 100 to 180 psia, and a total pressure of from 220 to 260 psia;

(b) separating reactor effluent into a hydrogen-rich gas stream and an adsorber feed stream;

(c) passing the adsorber feed stream to an adsorption section to adsorb normal hydrocarbons from said reactor effluent, and passing non-normal hydrocarbons out of the adsorption section as adsorber effluent containing an isomerate product;

(d) separating a hydrogen-containing feed gas, comprising a major proportion of hydrogen and a minor proportion of paraffinic hydrocarbons, into one stream comprising said essentially pure hydrogen and a second effluent containing paraffinic hydrocarbons;

(e) burning said second effluent to supply heat to at least one feed to said isomerization reactor; and (f) forming a hydrogen recycle stream having a hydrogen concentration of at least 80 mole percent and a concentration of light hydrocarbons of less than 20 mole percent by adding said essentially pure hydrogen to at least a portion of said hydrogen-rich gas stream in an amount sufficient to achieve said hydrogen partial pressure when recycled to said isomerization reactor;

(g) passing said hydrogen recycle stream through said adsorber bed to produce said desorption effluent which comprises hydrogen and normal hydrocarbons; and (h) passing said desorption effluent to said isomerization reactor.

47. A process according to claim 46 which further includes the step of controlling said hydrogen recycle stream and said adsorber feed stream flow rates to said adsorption section and the desorption effluent therefrom to provide said hydrogen partial pressure within said isomerization reactor.

48. A process according to claim 47 which further includes controlling the addition of essentially pure hydrogen to said hydrogen-rich gas stream to provide said hydrogen partial pressure within said isomerization reactor.

49. A process for utilizing reformer off gas and other impure hydrogen-containing refinery streams as a hydrogen source in a process for virtually complete isomerization of normal paraffin hydrocarbons in a feed stream containing normal and non-normal hydrocarbons, comprising:

(a) separating isomerization reactor effluent into a hydrogen-rich gas stream and an adsorber feed stream;

(b) passing a hydrogen-containing refinery gas stream, comprising paraffinic hydrocarbons, through a pressure swing adsorption system to yield essentially pure hydrogen and a second effluent containing paraffinic hydrocarbons;

(c) forming a hydrogen recycle stream by adding said essentially pure hydrogen to at least a portion of said hydrogen-rich gas stream in an amount sufficient to make up hydrogen lost during processing;

(d) passing said hydrogen recycle stream through an adsorber bed containing adsorbed normal hydrocarbon to produce a desorption effluent which comprises hydrogen and normal hydrocarbons; and (e) passing said desorption effluent to said isomerization reactor.

50. A process according to claim 49 wherein said hydrogen-containing refinery gas stream comprises less than 85 mole percent hydrogen.

51. A process according to claim 50 wherein said hydrogen-containing refinery gas stream comprises at least 15 mole percent light hydrocarbons and lesser amounts of hydrogen sulfide and chloride impurities.

52. A process according to claim 51 wherein said hydrogen-containing refinery gas stream is catalytic reformer off gas.

53. An apparatus for virtually complete isomerization of normal paraffin hydrocarbons in a feed stream containing normal and non-normal hydrocarbons, comprising:

(a) an isomerization reactor containing an isomerization catalyst;

(b) means for passing a combined reactor feed, through said isomerization reactor to convert at least a portion of the normal hydrocarbons in said reactor feed to non-normal hydrocarbons;

(c) means for withdrawing non-normal hydrocarbons from the reactor in a reactor effluent;

(d) means for separating reactor effluent into a hydrogen-rich gas stream and an adsorber feed stream;

(e) an adsorber section containing an adsorber bed capable of adsorbing normal hydrocarbons;

(f) means for passing the adsorber feed stream to said adsorption section to adsorb normal hydrocarbons from said reactor effluent;

(g) means for passing non-normal hydrocarbons out of said adsorption section as adsorber effluent containing an isomerate product;

(h) means for forming a hydrogen recycle stream by adding essentially pure hydrogen to at least a portion of said hydrogen-rich gas stream in an amount sufficient to achieve a hydrogen partial pressure which will protect said catalyst in said isomerization reactor when recycled to said reactor;

(i) means for passing said hydrogen recycle stream through said adsorber bed containing adsorbed normal hydrocarbons to produce said desorption effluent which comprises hydrogen and normal hydrocarbons; and (j) means for passing said desorption effluent to said isomerization reactor.

54. An apparatus according to claim 53 wherein said means for forming a hydrogen recycle stream by adding essentially pure hydrogen to at least a portion of said hydrogen-rich gas stream, comprises: a pressure swing adsorption apparatus, means for feeding reformer offgas to said pressure swing adsorption apparatus, and means for discharging essentially pure hydrogen from said pressure swing adsorption apparatus.

55. An apparatus for utilizing reformer off gas as a hydrogen source in a process for virtually complete isomerization of normal paraffin hydrocarbons in a feed stream containing normal and non-normal hydrocarbons, comprising:

(a) means for separating isomerization reactor effluent into a hydrogen-rich gas stream and an adsorber feed stream;

(b) a source of reformer off gas;

(c) means for passing a reformer off gas, comprising a major proportion of hydrogen and a minor proportion of paraffinic hydrocarbons, through a pressure swing adsorption system to yield essentially pure hydrogen and a second effluent containing paraffinic hydrocarbons;

(d) means for forming a hydrogen recycle stream by adding said essentially pure hydrogen to at least a portion of said hydrogen-rich gas stream in an amount sufficient to make up hydrogen lost during processing;

(e) means for passing said hydrogen recycle stream through an adsorber bed containing adsorbed normal hydrocarbon to produce a desorption effluent which comprises hydrogen and normal hydrocarbons; and (f) means for passing said desorption effluent to said isomerization reactor.

56. An apparatus according to claim 55 wherein said source of reformer off gas comprises means for passing said gas from a catalytic reformer capable of producing a hydrogen-containing gas stream containing less than 85 mole percent hydrogen and at least 15 mole percent light hydrocarbons.

* * * * *